United States Patent [19]
Heveling et al.

[11] Patent Number: 6,075,145
[45] Date of Patent: Jun. 13, 2000

[54] CATALYSTS CONTAINING ZIRCONIUM OXIDE

[75] Inventors: Josef Heveling, Naters, Switzerland; David Laffan, Cheshire, United Kingdom; Alain Wellig, Kanton Wallis, Switzerland

[73] Assignee: Lonza AG, Gampel/Valais, Switzerland

[21] Appl. No.: 09/035,839

[22] Filed: Mar. 6, 1998

[30] Foreign Application Priority Data

Mar. 7, 1997 [CH] Switzerland .......................... 0540/97
May 6, 1997 [CH] Switzerland .......................... 1059/97

[51] Int. Cl.$^7$ .............................................. C07D 453/02
[52] U.S. Cl. .............................................. 546/137
[58] Field of Search .............................. 546/137

[56] References Cited

U.S. PATENT DOCUMENTS

| | | | |
|---|---|---|---|
| 2,648,667 | 8/1953 | Sternbach | 568/880 |
| 4,511,455 | 4/1985 | Dosch et al. | 208/10 |
| 4,877,909 | 10/1989 | Mizusaki et al. | 568/880 |

FOREIGN PATENT DOCUMENTS

| | | | |
|---|---|---|---|
| 0 370 415 | 11/1989 | European Pat. Off. | 568/880 |
| 0596108 | 5/1994 | European Pat. Off. | 568/880 |
| 0603409 | 6/1994 | European Pat. Off. | 568/880 |
| WO 93/06098 | 4/1993 | WIPO | 568/880 |
| WO 98/00223 | 1/1998 | WIPO | 208/10 |

OTHER PUBLICATIONS

C.F. de Graauw, Laboratory of Organic Chemistry and Catalysis, Delft University of Technology, *Meerwein–Ponndorf–Verley Reductions and Oppenauer Oxidations: An Intergrated Approach.*

Makoto Shibagaki, The Chemical Society of Japan, (1988), vol. 61, PP 3283–3288, *The Catalytic Reduction of Aldehydes and Ketones with 2–Propanol over Hydrous Zirconium Oxide.*

Makoto Shibagaki, The Chemical Society of Japan, (1988), vol. 61, pp. 4153–4154, *The Hammett Relationship in the Reduction of Aldehuydes with 2–Prpanol by Catalysis wht Hydrous Zirconium Oxide.*

Makoto Shibagaki, The Chemical Society of Japan, (1990), vol. 63, No. 1, pp. 258–259, *The Catalytic Activitey of Hydrous Zirconium Oxide Calcined at Several Temperatures.*

Hideyuki Kuno, The Chemical Society of Japan, (1990), vol. 63, pp. 1943–1946, *Oxidation of Secondary Alcohols over Hydrous Zirconium(IV) Oxide.*

Hideyuki Kuno, The Chemical Society of Japan, (1991), vol. 64. No. 1, pp. 312–314, *Oxidation of Primary Alcohols over Hydrous Zirconium(IV) Oxide.*

*Primary Examiner*—John Kight
*Assistant Examiner*—Raymond Covington
*Attorney, Agent, or Firm*—Fisher, Christen & Sabol

[57] ABSTRACT

Catalyst compositions based on amorphous partially dehydrated zirconium hydroxide which are doped with from 0.01 to 20 atom percent of copper and/or from 0.01 to 20 atom percent of nickel, in each case based on zirconium, and have a specific surface area by the BET method of at least 50 m$^2$/g. The catalyst compositions are suitable, in particular, as the catalyst in hydrogen transfer reactions, such as, the Meerwein-Ponndorf-Verley reduction or the Oppenauer oxidation. The preparation of 3-hydroxyquinuclidine of the formula:

I

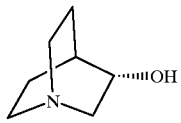

involves reaction of quinuclidin-3-one with a secondary alcohol in the presence of the amorphous partially dehydrated zirconium hydroxide.

7 Claims, No Drawings

CATALYSTS CONTAINING ZIRCONIUM OXIDE

BACKGROUND OF THE INVENTION

1. Field of the Invention

The invention relates to catalysts based on amorphous partially dehydrated zirconium hydroxide ($ZrO_2 \cdot xcH_2O$), a process for their preparation and also their use in hydrogen transfer reactions between carbonyl compounds and alcohols, in particular the Meerwein-Ponndorf-Verley reduction and the Oppenauer oxidation. The invention further relates to a process for preparing 3-hydroxyquinuclidine of the formula:

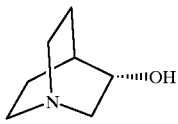

I by reduction of quinuclidin-3-one of the formula:

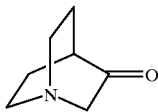

It is known that the hydrogen transfer reactions between aldehydes or ketones and primary or secondary alcohols which are usually carried out under the catalytic action of aluminum alkoxides and summarized under the names "Meerwein-Ponndorf-Verley reduction" and "Oppenauer oxidation" can also be carried out under heterogeneous catalysis [C. F. de Graauw et al., *Synthesis*, (1994), 1007–1017]. Owing to the easier work-up of the reaction mixture and the fact that the catalyst may possibly be reused, this variant is of great interest. As the heterogeneous catalyst, use has been made, inter alia, of partially dehydrated zirconium hydroxide (hydrous zirconium oxide) [M. Shibagaki et al., *Bull. Chem. Soc. Jpn.*, (1988), 61, 3283–3288; *Bull. Chem. Soc. Jpn.*, (1988), 61, 4153–4154; and *Bull. Chem. Soc. Jpn.*, (1990), 63, 258–259; and H. Kuno et al., *Bull. Chem. Soc. Jpn.*, (1990), 63, 1943–1946; and *Bull. Chem. Soc. Jpn.*, (1991), 63, 312–314]. However, the activity of this catalyst is not very high, so that, particularly when using relatively unreactive carbonyl compounds and/or alcohols, only moderate or poor yields are frequently obtained.

3-Hydroxyquinuclidine is a starting material for the synthesis of various pharmaceutically active compounds such as choline mimetics (U.S. Pat. No. 2,648,667, and European Published Patent Application No. 0370415) or bronchodilators (WO-A-93/06,098). Various methods are known for preparing 3-hydroxyquinuclidine from quinuclidin-3-one (U.S. Pat. No. 2,648,667), namely, the hydrogenation of the hydrochloride using platinum oxide as the catalyst, the reduction of the hydrochloride using sodium/ethanol, the hydrogenation of the free base using platinum oxide or Raney nickel as the catalyst, and also the reduction of the free base with lithium aluminum hydride. However, none of these methods is free of disadvantages. Platinum oxide is very expensive, Raney nickel is pyrophoric and both sodium/ethanol and lithium aluminum hydride as reducing agent lead to safety and waste problems when employed on an industrial scale.

BROAD DESCRIPTION OF THE INVENTION

An object of the invention is to provide a more active heterogeneous catalyst for the Meerwein-Ponndorf-Verley reduction and the Oppenauer oxidation. Another object of the invention is to provide an alternative process for preparing 3-hydroxyquinuclidine, which process is suitable for implementation on an industrial scale, gives little waste and requires neither high pressure nor expensive or hazardous reagents. Other objects and advantages of the invention are set out herein or are obvious herefrom to one skilled in the art.

The objects and advantages of the invention are achieved by means of the catalysts of the invention and the process for preparing 3-hydroxyquinuclidine of the invention.

It has been found that the activity of amorphous, partially dehydrated zirconium hydroxide having a specific surface area by the BET method of at least 50 $m^2/g$ can be considerably increased by doping with from 0.01 to 20 atom percent (based on Zr) of copper and/or nickel.

The catalyst compositions according to the invention preferably correspond to the formula:

III wherein, $0 \leq a \leq 0.2$, $0 \leq b \leq 0.2$ and $0.2 \leq x \leq 2.0$, with the proviso that $a+b \geq 0.0001$. Particularly preferred catalyst compositions are those in which $a \leq 0.15$, $b \leq 0.1$, $a+b \geq 0.0002$ and $0.3 \leq x \leq 2.0$. Very particular preference is given to those catalyst compositions in which either copper or nickel is not present, i.e., in which either $a=0$ or $b=0$.

The specific surface area by the BET method of the catalyst compositions of the invention is preferably greater than 100 $m^2/g$; particular preference is given to catalyst compositions having a specific surface area of more than 150 $m^2/g$.

The catalyst compositions of the invention can be prepared, for example, by precipitating zirconium hydroxide from an aqueous solution of a zirconium salt by addition of a base, calcining the zirconium hydroxide at from 200° to 400° C. and subsequently impregnating it with a solution of a copper and/or nickel salt and drying it.

The zirconium salt used is preferably zirconyl chloride ($ZrOCl_2$) and the base used is preferably an aqueous solution of ammonia or an aqueous alkali metal hydroxide solution, such as, sodium hydroxide solution. As the copper and/or nickel salt, preference is given to using the corresponding nitrate.

The calcination temperature is preferably from 250° to 350° C., particularly preferably from 270° to 320° C.

The catalyst compositions of the invention are suitable as the catalyst for the reduction of aldehydes or ketones to the corresponding primary or secondary alcohols by hydrogen transfer from a secondary alcohol as the hydrogen donor (Meerwein-Ponndorf-Verley reduction). The hydrogen donor used here is preferably isopropyl alcohol.

The catalyst compositions of the invention are likewise suitable as the catalyst for the oxidation of primary or secondary alcohols to the corresponding aldehydes or ketones by hydrogen transfer to a ketone or quinone as the hydrogen acceptor (Oppenauer oxidation). As the hydrogen acceptor, preference is given to using cyclohexanone or p-benzoquinone.

The catalyst compositions of the invention can be readily used a plurality of times without any appreciable loss in activity occurring or a significant part of the doping being lost.

It has also been found that quinuclidin-3-one or a corresponding salt, such as, quinuclidin-3-one hydrochloride, can be reduced by means of a secondary alcohol as the hydrogen donor in the presence of amorphous, partially dehydrated zirconium hydroxide ($ZrO_2.xH_2O$) in the manner of a Meerwein-Ponndorf-Verley reduction to give a good yield of 3-hydroxyquinuclidine or the corresponding salt. If the reduction is carried out using a salt of quinuclidin-3-one, the resulting 3-hydroxyquinuclidine salt can, if desired, be converted into the free 3-hydroxyquinuclidine by addition of a strong base during the work-up of the reaction mixture.

The amorphous partially dehydrated zirconium hydroxide can be prepared, for example, by precipitation of zirconium hydroxide from an aqueous zirconium salt solution and subsequent calcination at low temperature. A suitable zirconium salt solution is, for example, a zirconyl chloride solution; a suitable precipitant is, for example, an alkali metal hydroxide solution. The calcination can be carried out, for example, at 270° to 320° C.

In the process of the invention, the secondary alcohol used is preferably isopropyl alcohol. This is dehydrogenated to acetone in the process. Since the reaction is an equilibrium reaction, the secondary alcohol is preferably used in excess in order to shift the equilibrium in the desired direction. The excess secondary alcohol can simultaneously serve as solvent.

The reaction is preferably carried out at a temperature of 120° to 220° C., particularly preferably at 150° to 200° C., in the liquid phase. If the secondary alcohol used has a boiling point at atmospheric pressure below the reaction temperature, the reaction is advantageously carried out at superatmospheric pressure in an autoclave or another suitable pressure vessel.

After the reaction is complete, the catalyst can be separated off very simply by filtration and (if appropriate after a washing procedure) can be reused without any great loss in activity.

DETAILED DESCRIPTION OF THE INVENTION

The following examples illustrate the invention without constituting a restriction.

EXAMPLE 1

Preparation of $ZrO_2.xH_2O$

In a flow-through reactor equipped with a high-speed stirrer (Ultra-Turrax®, 9000 min$^{-1}$), zirconyl chloride solution (265 g/l, calculated as $ZrO_2$) was precipitated semicontinuously using sodium hydroxide solution (30 percent). The addition rate of the zirconyl chloride solution was set such that 50 kg of $ZrO_2$ was introduced over a period of 5 hours. The sodium hydroxide solution was added via a metering pump at such a rate that the precipitation took place at a constant pH of 8.0. Since this required less than the stoichiometric amount of NaOH, the remainder of the stoichiometric amount was added to the resulting zirconium hydroxide suspension after the precipitation. The suspension was subsequently dewatered in a chamber filter press and the filter cake was washed with deionized water until neutral and free of chloride. The washed filter cake was dried at 100° C. and then introduced into water, whereupon the pieces of filter cake broke up into small pieces. These were dried again at 100° C. and subsequently heated at 30 K/h to 300° C. and calcined at this temperature for 8 hours. The product thus obtained was X-ray-amorphous, had a specific surface area by the BET method of 196 m$^2$/g and a pore volume of 0.43 cm$^3$/g.

EXAMPLE 2

Preparation of $ZrO_2.xH_2O$

The procedure was as described in Example 1, but the calcination temperature was only 270° C. The product thus obtained was X-ray-amorphous, had a specific surface area by the BET method of 212 m$^2$/g and a pore volume of 0.41 cm$^3$/g. The water content determined by thermogravimetric analysis corresponded to the formula $ZrO_2.0.57H_2O$. At 430° C., it transformed exothermically into a crystalline form.

EXAMPLE 3

Preparation of $ZrO_2.xH_2O$

Zirconyl chloride octahydrate ($ZrOCl_2.8H_2O$) was dissolved in water. The slight turbidity was filtered off and the filtrate was adjusted to a concentration of 50 g/l (calculated as $ZrO_2$) using deionized water. 2.5 l of deionized water were placed in a reaction vessel fitted with a high-speed stirrer. While stirring vigorously (8000 min$^{-1}$), 50 ml/min of the zirconyl chloride solution was metered in simultaneously with sufficient 10 percent strength ammonia solution to maintain a pH of 7.0±0.2 during the resulting precipitation. At the same time, deionized water was added in an amount sufficient to prevent the solids content of the suspension from exceeding about 1 percent. After the precipitation was complete, the solid was separated off by filtration and the filter cake was washed with ammonia water until the chloride content had dropped to 0.05 percent. The washed filter cake was dried at 100° C., slurried once more in water and again filtered and dried. The zirconium oxide hydrate thus obtained was calcined for 8 hours at 300° C. The product thus obtained was X-ray-amorphous and had a specific surface area by the BET method of 240 m$^2$/g.

EXAMPLE 4

$Cu_{0.03}ZrO_{2.03}.0.61H_2O$ 20 g of $ZrO_2.xH_2O$ from Example 3 was treated twice with 40 ml each time of a 1.027 M copper(II) nitrate solution for 16 hours each time and after each treatment was washed ten times with water and dried for 12 hours at 120° C./30 mbar. The catalyst composition thus obtained had a copper content of 1.4 percent by weight and a loss on ignition of 8.1 percent, corresponding to the formula $Cu_{0.03}ZrO_{2.03}.0.61H_2O$. The specific surface area by the BET method was 247 m$^2$/g and the pore volume was 0.24 cm$^3$/g. Crystallization commenced at 497° C.

EXAMPLE 5

$Ni_{0.013}ZrO_{2.013}.0.62H_2O$

The procedure was as described in Example 4, but 200 ml of 0.5 M nickel(II) nitrate solution was used in place of the copper(II) nitrate solution and the duration of the first treatment was shortened to 2 hours. The solid was washed 15 times with water after the first treatment and seven times after the second treatment. The catalyst composition thus obtained had a nickel content of 0.6 percent by weight and a loss on ignition of 8.2 percent, corresponding to the formula $Ni_{0.013}ZrO_{2.013}.0.62H_2O$. The specific surface area by the BET method was 248 m$^2$/g and the pore volume was 0.23 cm$^3$/g. Crystallization commenced at 495° C.

EXAMPLE 6

$Cu_{0.0047}ZrO_{2.0047}.0.39H_2O$

In a 1000 ml flask, 100 g of $ZrO_2.xH_2O$ (prepared as described in Example 1) was mixed with 400 ml of a 0.276

M copper(II) nitrate solution for 72 hours while rotating slowly (rotary evaporator). Subsequently, the catalyst suspension thus obtained was filtered on a suction filter and the filter cake was slurried with deionized water 25 times and filtered again each time. The filter cake was subsequently extracted with deionized water for 72 hours in a Soxhlet extractor and finally dried for 24 hours at 120° C./30 mbar. The catalyst composition thus obtained had a copper content of 0.23 percent by weight and a loss on ignition of 5.4 percent, corresponding to the formula $Cu_{0.0047}ZrO_{2.0047} \cdot 0.39H_2O$. The specific surface area by the BET method was 219 m$^2$/g and the pore volume was 0.44 cm$^3$/g. Crystallization commenced at 408° C.

EXAMPLE 7

$Ni_{0.00022}ZrO_{2.00022} \cdot 0.35H_2O$

The procedure was as described in Example 6, but a 0.256 M nickel(II) nitrate solution was used in place of the copper(II) nitrate solution. The catalyst composition thus obtained had a nickel content of 0.01 percent by weight and a loss on ignition of 4.9 percent, corresponding to the formula $Ni_{0.00022}ZrO_{2.00022} \cdot 0.35H_2O$. The specific surface area by the BET method was 217 m$^2$/g and the pore volume was 0.44 cm$^3$/g. Crystallization commenced at 404° C.

EXAMPLE 8

$Cu_{0.016}ZrO_{2.016} \cdot 0.5H_2O$ 50 g of $ZrO_2 \cdot xH_2O$ from Example 2 was treated twice with 200 ml each time of a 0.505 M copper(II) nitrate solution for 24 hours each time, washed five times with water after each treatment and finally dried for 24 hours at 120° C./30 mbar. The catalyst composition thus obtained had a copper content of 0.74 percent by weight and a loss on ignition of 6.8 percent, corresponding to the formula $Cu_{0.016}ZrO_{2.016} \cdot 0.5H_2O$. The specific surface area by the BET method was 214 m$^2$/g and the pore volume was 0.41 cm$^3$/g. Crystallization commenced at 456° C.

EXAMPLE 9

$Cu_{0.053}ZrO_{2.053} \cdot 1.35H_2O$ 100 g of $ZrO_2 \cdot xH_2O$ (type XZO 631/02 from MEL Chemicals, Manchester, UK; specific surface area by the BET method=210 m$^2$/g, pore volume=0.12 cm$^3$/g, crystallization from 419° C.) was treated with 200 ml of a 0.513 M copper(II) nitrate solution for 24 hours, then washed six times with water and finally dried for 24 hours at 100° C./30 mbar. The catalyst composition thus obtained had a copper content of 2.17 percent by weight and a loss on ignition of 16.0 percent, corresponding to the formula $Cu_{0.053}ZrO_{2.053} \cdot 1.35H_2O$. The specific surface area by the BET method was 274 m$^2$/g and the pore volume was 0.12 cm$^3$/g. Crystallization commenced at 508° C.

EXAMPLE 10

$Cu_{0.067}ZrO_{2.067} \cdot 1.40H_2O$

The procedure was as described in Example 9, but 250 g of $ZrO_2 \cdot xH_2O$ and 500 ml of 0.513 M copper(II) nitrate solution were used. The number of times the solid was washed was reduced to five. The catalyst composition thus obtained had a copper content of 2.75 percent by weight. The loss on ignition of 16.4 percent corresponded to the formula $Cu_{0.067}ZrO_{2.067} \cdot 1.40H_2O$. The specific surface area by the BET method was 229 m$^2$/g and the pore volume was 0.10 cm$^3$/g. Crystallization commenced at 520° C.

EXAMPLE 11

$Cu_{0.14}ZrO_{2.14} \cdot 1.90H_2O$

The procedure was as described in Example 9, but 50 g of $ZrO_2 \cdot xH_2O$ and 120 ml of 0.529 M copper(II) nitrate solution were used. The product was not washed. The catalyst composition thus obtained had a copper content of 5.30 percent by weight and a loss on ignition of 20.3 percent, corresponding to the formula $Cu_{0.14}ZrO_{2.14} \cdot 1.90H_2O$. The specific surface area by the BET method was 229 m$^2$/g and the pore volume was 0.10 cm$^3$/g. Crystallization commenced at 564° C.

EXAMPLES 12 AND 13

Comparative Example 1 trans-2-Hexenol (Meerwein-Ponndorf-Verley reduction)

In a round-bottomed flask provided with magnetic stirrer and reflux condenser, 0.5 g (5.1 mmol) of trans-2-hexenal, 12 g of isopropyl alcohol and 3.9 g of catalyst were heated under reflux. After the end of the reaction time, the reaction mixture was analyzed by gas chromatography and the yield was determined. The results are summarized in Table 1 below:

TABLE 1

| Example No. | Catalyst | Reaction time [h] | Yield [%] |
|---|---|---|---|
| C1 | From Example 3 (undoped) | 8 | 77.4 |
| 12 | from Example 4 | 7 | 88.0 |
| 13 | from Example 5 | 7 | 79.2 |

EXAMPLES 14 TO 20

Comparative Examples 2 and 3

Cinnamic alcohol (Meerwein-Ponndorf-Verley reduction)

In a three-necked flask provided with reflux condenser and magnetic stirrer, 0.5 g (3.8 mmol) of cinnamaldehyde (trans-3-phenyl-2-propanol) and 12 g of isopropyl alcohol (for a starting material/catalyst ratio=1:1) or 1.5 g (11.3 mmol) of cinnamaldehyde and 36 g of isopropyl alcohol (starting material/catalyst=3:1) were refluxed under argon with 0.5 g of catalyst and 1.5 g of dodecane (as GC standard). After the end of the reaction time, the reaction mixture was analyzed by gas chromatography and the yield was determined. The results are summarized in Table 2 below:

TABLE 2

| Example No. | Catalyst | Reaction time [h] | Yield [%] | Starting material/catalyst |
|---|---|---|---|---|
| C2 | from Example 1 (undoped) | 24 | 63.8 | 1:1 |
| C3 | MEL*) (undoped) | 24 | 44.5 | 3:1 |
| 14 | from Example 6 | 24 | 72.4 | 1:1 |

TABLE 2-continued

| Example No. | Catalyst | Reaction time [h] | Yield [%] | Starting material/catalyst |
|---|---|---|---|---|
| 15 | from Example 4 | 24 | 97.3 | 1:1 |
| 16 | from Example 9 | 22.3 | 100.0 | 3:1 |
| 17 | from Example 9 | 19.2 | 98.5 | 3:1 |
| 18 | from Example 10 | 6.5 | 100.0 | 3:1 |
| 19 | from Example 11 | 3.3 | 99.5 | 3:1 |
| 20 | from Example 5 | 24 | 89.3 | 1:1 |

*)Type XZO 631/02, MEL Chemicals, Manchester, UK($ZrO_2 \cdot xH_2O$)

EXAMPLES 21 TO 23

Comparative Example 4

1-(p-Chlorophenyl)ethanol (Meerwein-Ponndorf-Verley reduction)

In a round-bottomed flask provided with magnetic stirrer and reflux condenser or in a 100 ml autoclave, 5.0 g (32.3 mmol) of p-chloroacetophenone, 45 g of isopropyl alcohol and 1.0 g of catalyst were heated under reflux or at 120° C. After the end of the reaction time, the reaction mixture was analyzed by gas chromatography and the yield was determined. The results are summarized in Table 3 below:

TABLE 3

| Example No. | Catalyst | Reaction time*) [h] | Yield [%] |
|---|---|---|---|
| C4 | From Example 1 (undoped) | 24 (R) | 22.5 |
| 21 | From Example 4 | 24 (R) | 38.9 |
| 22 | From Example 9 | 24 (R) | 69.7 |
| 23 | From Example 9 | 16 (A) | 94.2 |

*)(R) = reflux; (A) = autoclave

The experiment of Example 22 was also repeated a further five times using the same catalyst sample, with the copper content of the catalyst being checked after each repetition. Neither a significant yield change nor a reduction in the copper content of the catalyst was observed.

EXAMPLES 24 AND 25

Comparative Example 5

3-Methyl-2-buten-1-ol (Meerwein-Ponndorf-Verley reduction)

In a round-bottomed flask provided with magnetic stirrer and reflux condenser or in a 100 ml autoclave, 3.0 g (35.7 mmol) of 3-methyl-2-butenal, 72 g of isopropyl alcohol and 1.0 g of catalyst were heated under reflux or at 110° C. After the end of the reaction time, the reaction mixture was analyzed by gas chromatography and the yield was determined. The results are summarized in Table 4 below:

TABLE 4

| Example No. | Catalyst | Reaction time*) [h] | Yield [%] |
|---|---|---|---|
| C5 | From Example 2 (undoped) | 24 (R) | 3.8 |
| 24 | From Example 10 | 30 (R) | 86.5 |
| 25 | From Example 10 | 18 (A) | 91.5 |

*)(R) = reflux; (A) = autoclave

EXAMPLES 26 AND 27

Comparative Example 6

Cinnamaldehyde (Oppenauer oxidation)

1.5 g (11.2 mmol) of cinnamyl alcohol (trans-3-phenyl-2-propen-1-ol), 36 g (367 mmol) of cyclohexanone, 0.5 of catalyst and 1.5 g of dodecane (as GC standard) were heated under argon. After the end of the reaction time, the reaction mixture was analyzed by gas chromatography and the yield was determined. The results are summarized in Table 5 below:

TABLE 5

| Example No. | Catalyst | Reaction time [h] | Temperature [° C.] | Yield [%] |
|---|---|---|---|---|
| C6 | MEL*) (undoped) | 24 | 100° | 37.1 |
| 26 | from Example 10 | 24 | 60° | 56.4 |
| 27 | from Example 9 | 5.5 | 120° | 67.2 |

*)Type XZO 631/02, MEL Chemicals, Manchester, UK($ZrO_2 \cdot xH_2O$)

EXAMPLE 28

Acetophenone (Oppenauer oxidation)

5.0 g (40.9 mmol) of 1-phenylethanol, 15.0 g (153 mmol) of cyclohexanone and 1.0 g of catalyst from Example 9 in 30 g of toluene were heated at 70° C. under argon. After a reaction time of 10 hours, the reaction mixture was analyzed by gas chromatography. The yield of product was 94.2 percent.

EXAMPLE 29

Comparative Example 7

Benzaldehyde (Oppenauer oxidation)

1.5 g (13.9 mmol) of benzyl alcohol, 3.0 g (27.8 mmol) of p-benzoquinone and 0.5 g of catalyst in 26 g of 1,4-dioxane were refluxed under argon. After a reaction time of 24 hours, the yield was determined by gas chromatography. The yield obtained using the catalyst according to the invention from Example 10 was 55.6 percent; and a yield of only 23.6 percent was obtained using the undoped catalyst from Example 2, which is not according to the invention.

EXAMPLE 30

3-Hydroxyquinuclidine

A 100 ml autoclave ("Magnedrive II", Autoclave Engineers Europe) fitted with a hollow-shaft high-speed stirrer (Dispersimax®) was charged with 5.0 g of quinuclidin-3-one (prepared from the hydrochloride by reaction with sodium methoxide and extraction with diethyl ether), 45 ml of isopropyl alcohol and 0.25 g of catalyst (from Example 1), flushed with nitrogen and placed under a nitrogen pressure of 10 bar at room temperature. While stirring (1500 min$^{-1}$), the mixture was heated to 200° C. and held at this temperature for 8 hours. The yield was determined as 97.3 percent by means of GC. Repeating the experiment using the same catalyst still gave a yield of 92.8 percent after a reaction time of 13 hours.

EXAMPLE 31

3-Hydroxyquinuclidine

In an autoclave, 81.6 g (0.496 mol) of quinuclidin-3-one hydrochloride and 12.4 g of catalyst (from Example 1) were suspended in 800 ml of isopropyl alcohol while stirring vigorously. The autoclave was closed and the air present was displaced by argon under atmospheric pressure. The autoclave was then heated to an internal temperature of 150° C., whereupon a pressure of 6 to 8 bar was established, and held at this temperature for 7 hours. After cooling to room temperature, 89.5 g of a 30 percent strength solution of sodium methoxide in methanol was added. The mixture was stirred further for 45 minutes and then filtered. The filtrate was evaporated under reduced pressure and the residue was recrystallized hot from 640 ml of toluene. The catalyst was washed until free of salt and dried, after which it could be reused. The yield of the catalyst was 59.2 g (93 percent), and the assay (GC) of the catalyst was 99 percent.

What is claimed is:

1. A process for preparing 3-hydroxyquinuclidine of formula:

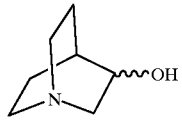

I or a corresponding salt, comprising reducing quinuclidin-3-one of formula:

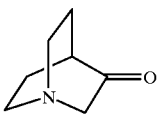

II or a corresponding salt, by reacting the quinuclidin-3-one of formula II with a secondary alcohol as hydrogen donor in the presence of amorphous partially dehydrated zirconium hydroxide.

2. The process according to claim 1, wherein the secondary alcohol is isopropyl alcohol.

3. The process according to claim 2, wherein the reaction is carried out at 120° to 220° C., in the liquid phase.

4. The process according to claim 1, wherein the reaction is carried out at 120° to 220° C. in the liquid phase.

5. The process according to claim 1, wherein the reaction is carried out at 150° to 200° C. in the liquid phase.

6. The process as claimed in claim 1 wherein an excess of the secondary alcohol is present thereby simultaneously serving as solvent.

7. The process as claimed in claim 1 wherein, if the secondary alcohol has a boiling point at atmospheric pressure below the reaction temperature, the reaction is carried out at superatmospheric pressure.

* * * * *